United States Patent [19]

Amschler

[11] Patent Number: 5,712,298
[45] Date of Patent: Jan. 27, 1998

[54] FLUOROALKOXY-SUBSTITUTED BENZAMIDES AND THEIR USE AS CYCLIC NUCLEOTIDE PHOSPHODIESTERASE INHIBITORS

[75] Inventor: Hermann Amschler, Radolfzell, Germany

[73] Assignee: BYK Gulden Lomberg Chemische Fabrik GmbH, Konstanz, Germany

[21] Appl. No.: 564,322

[22] PCT Filed: Jul. 2, 1994

[86] PCT No.: PCT/EP94/02169

§ 371 Date: Dec. 19, 1995

§ 102(e) Date: Dec. 19, 1995

[87] PCT Pub. No.: WO95/01338

PCT Pub. Date: Jan. 12, 1995

[30] Foreign Application Priority Data

Jul. 2, 1993 [CH] Switzerland ............... 01 996/99

[51] Int. Cl.⁶ ............ C07D 213/75; C07C 235/56; A61K 31/44; A61K 31/165
[52] U.S. Cl. ............ 514/352; 514/617; 546/309; 564/170
[58] Field of Search ............ 546/309; 564/170; 514/352, 617

[56] References Cited

U.S. PATENT DOCUMENTS 5,340,827  8/1994  Beeley et al. ............ 514/352

FOREIGN PATENT DOCUMENTS 0120352  3/1984  European Pat. Off. .
9212961  8/1992  WIPO .

OTHER PUBLICATIONS

Fialkov et al., Chemical Abstracts, vol. 98, No. 23, Abstract 197,713n, Jun. 6, 1983, p. 603.
Yagupolskŭet al., Chemical Abstracts, vol. 55, No. 18 Abstract 17.563i Sep. 4, 1961.
Hahn, Chemical Abstracts, vol. 58, No. 9, Abstract 8944b/c, Apr. 29, 1963.

*Primary Examiner*—Zinna Northington Davis
*Attorney, Agent, or Firm*—Jacobson, Price, Holman, & Stern, PLLC

[57] ABSTRACT

Compounds of formula (I), in which one of the substituents R1 or R2 stands for hydrogen, 1–6C-alkoxy, 3–7C-cycloalkoxy, 3–7C-cycloalkylmethoxy, benzyloxy or totally or partially fluorine-substituted 1–4C-alkoxy, and the other stands for totally or partially fluorine-substituted 1–4C-alkoxy, and R3 stands for phenyl, pyridyl, R31, R32 and R33-substituted phenyl or R34, R35, R36 and R37-substituted pyridyl, in which R31 stands for hydroxy, halogen, cyano, carboxyl, trifluoromethyl 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino; R32 stands for hydrogen, hydroxy, halogen, amino, trifluoromethyl, 1–4C-alkyl or 1–4C-alkoxy; R33 stands for hydrogen, halogen, 1–4C-alkyl or 1–4C-alkoxy; R34 stands for hydroxy, halogen, cyano, carboxyl, 1–4C-alkyl, 1–4C-alkoxy, 1–4C-alkoxycarbonyl or amino; R35 stands for hydrogen, halogen, amino or 1–4C-alkyl; R36 stands for hydrogen or halogen; and R37 stands for hydrogen or halogen. These compounds constitute new effective bronchotherapeutic drugs.

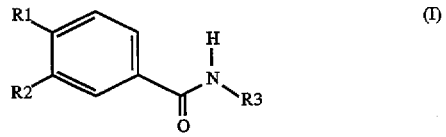

8 Claims, 1 Drawing Sheet

FLUOROALKOXY-SUBSTITUTED BENZAMIDES AND THEIR USE AS CYCLIC NUCLEOTIDE PHOSPHODIESTERASE INHIBITORS

CONTINUING DATA

This Application is a §371 of PCT/EP94/02169, filed Jul. 2, 1994.

FIELD OF APPLICATION OF THE INVENTION

The invention relates to novel fluoroalkoxy-substituted benzamides, which are used in the pharmaceutical industry for the production of medicaments.

KNOWN TECHNICAL BACKGROUND

International Patent Application WO92/12961 describes benzamides having PDE-inhibiting properties. International Patent Application WO93/25517 discloses trisubstituted phenyl derivatives as selective PDE-IV inhibitors. International Patent Application WO94/02465 describes inhibitors of c-AMP phosphodiesterase and of TNF.

DESCRIPTION OF THE INVENTION

It has now been found that the benzamides which are described in greater detail below, which differ from the previously published compounds in particular by the fluoroalkoxy substitution in the 3- or 4-position on the benzamide, have surprising and particularly advantageous properties.

Figure 1:
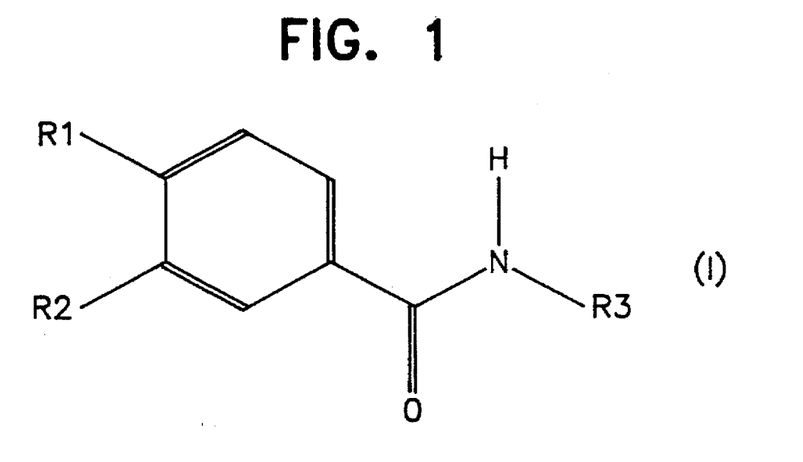
FIGS. 1 and 2 are respective formulae of compounds represented thereby.

The invention thus relates to compounds of the formula I, in which
  one of the substituents R1 and R2 is hydrogen, 1–6C-alkoxy, 3–7C-cycloalkoxy, 3–7C-cycloalkylmethoxy, benzyloxy or 1–4C-alkoxy which is completely or partially substituted by fluorine, and the other is 1–4C-alkoxy which is completely or partially substituted by fluorine, and
  R3 is phenyl, pyridyl, phenyl which is substituted by R31, R32 and R33 or pyridyl which is substituted by R34, R35, R36 and R37, where
    R31 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino,
    R32 is hydrogen, hydroxyl, halogen, amino, trifluoromethyl, 1–4C-alkyl or 1–4C-alkoxy,
    R33 is hydrogen, halogen, 1–4C-alkyl or 1–4C-alkoxy,
    R34 is hydroxyl; halogen, cyano, carboxyl, alkyl, 1–4C-alkoxy, 1–4C-alkoxycarbonyl or amino,
    R35 is hydrogen, halogen, amino or 1–4C-alkyl,
    R36 is hydrogen or halogen and
    R37 is hydrogen or halogen,
the salts of these compounds, and the N-oxides of the pyridines and their salts.

One embodiment (embodiment a) of the invention consists of compounds of the formula I, in which
  one of the substituents R1 and R2 is hydrogen, 1–6C-alkoxy, 3–7C-cycloalkoxy, 3–7C-cycloalkylmethoxy, benzyloxy or 1–4C-alkoxy which is completely or partially substituted by fluorine, and the other is 1–4C-alkoxy which is completely or partially substituted by fluorine, and
  R3 is phenyl, pyridyl, phenyl which is substituted by R31, R32 and R33 or pyridyl which is substituted by R34, R35, R36 and R37, where
    R31 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino,
    R32 is hydrogen, hydroxyl, halogen, amino, trifluoromethyl, 1–4C-alkyl or 1–4C-alkoxy,
    R33 is hydrogen, halogen, 1–4C-alkyl or 1–4C-alkoxy,
    R34 is hydroxyl, halogen, cyano, carboxyl, 1–4C-alkyl, 1–4C-alkoxy, 1–4C-alkoxycarbonyl or amino,
    R35 is hydrogen, halogen, amino or 1–4C-alkyl,
    R36 is hydrogen or halogen and
    R37 is hydrogen or halogen,
the salts of these compounds, and the N-oxides of the pyridines and their salts, where those compounds are excluded in which R1 is 1–4C-alkoxy which is completely or partially substituted by fluorine and R2 is 3–7C-cycloalkoxy.

A further embodiment (embodiment b) of the invention are compounds of the formula I, in which either
  R1 is 1–4C-alkoxy which is completely or partially substituted by fluorine and
  R2 is methoxy,
or
  R1 is hydrogen, 1–6C-alkoxy, 3–7C-cycloalkoxy, 3–7C-cycloalkylmethoxy, benzyloxy or 1–4C-alkoxy which is completely or partially substituted by fluorine and
  R2 is methoxy which is completely or partially substituted by fluorine,
or
  R1 is 3–7C-cycloalkoxy, 3–7C-cycloalkylmethoxy or benzyloxy and
  R2 is 1–4C-alkoxy which is completely or partially substituted by fluorine,
or
  R1 is 1–4C-alkoxy which is completely or partially substituted by fluorine and
  R2 is 3–7C-cycloalkylmethoxy or benzyloxy,
and
  R3 is phenyl, pyridyl, phenyl which is substituted by R31, R32 and R33 or pyridyl which is substituted by R34, R35, R36 and R37, where
    R31 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino,
    R32 is hydrogen, hydroxyl, halogen, amino, trifluoromethyl, 1–4C-alkyl or 1–4C-alkoxy,
    R33 is hydrogen, halogen, 1–4C-alkyl or 1–4C-alkoxy,
    R34 is hydroxyl, halogen, cyano, carboxyl, 1–4C-alkyl, 1–4C-alkoxy, 1–4C-alkoxycarbonyl or amino,
    R35 is hydrogen, halogen, amino or 1–4C-alkyl,
    R36 is hydrogen or halogen and
    R37 is hydrogen or halogen,
the salts of these compounds, and the N-oxides of the pyridines and their salts.

1–6C-Alkoxy is a radical which, in addition to the oxygen atom, contains a straight-chain or branched alkyl radical having 1 to 6 carbon atoms. Alkyl radicals having 1 to 6 carbon atoms which may be mentioned in this context are, for example, the hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkoxy is, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy is, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

1–4C-Alkoxy which is completely or partially substituted by fluorine is, for example, the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radical.

Halogen within the meaning of the present invention is bromine, chlorine and fluorine.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which, an addition to the oxygen atom, contains one of the abovementioned 1–4C-alkyl radicals. Examples are the methoxy and the ethoxy radicals.

1–4C-Alkoxycarbonyl is a carbonyl group to which one of the abovementioned 1–4C-alkoxy radicals is bonded. Examples are the methoxycarbonyl ($CH_3O$—CO—) and the ethoxycarbonyl radical ($CH_3CH_2O$—CO—).

1–4C-Alkylcarbonyl is a carbonyl group to which one of the abovementioned 1–4C-alkyl radicals is bonded. An example is the acetyl radical ($CH_3CO$—).

1–4C-Alkylcarbonyloxy radicals contain, in addition to the oxygen atom, one of the abovementioned 1–4C-alkylcarbonyl radicals. An example is the acetoxy radical ($CH_3CO$—O—).

Mono- or di-1–4C-alkylamino radicals are, for example, the methylamino, the dimethylamino and the diethylamino radicals.

A 1–4C-alkylcarbonylamino radical is, for example, the acetamido radical (—NH—CO—$CH_3$).

Exemplary phenyl radicals substituted by R31, R32 and R33 are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxyphenyl, 2,4-dimethoxyphenyl, 2,6-dimethoxyphenyl, 2-dimethylaminophenyl, 2-methylphenyl, 2-chloro-6-methylphenol, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Exemplary pyridyl radicals substituted by R34, R35, R36 and R37 are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trifluoropyrid-4-yl and 2,3,5-trifluoropyrid-4-yl.

Suitable salts for compounds of the formula I—depending on substitution—are all acid addition salts, but in particular all salts with bases. Particular mention may be made of the pharmacologically tolerable. inorganic and organic acids and bases customarily used in pharmacy. Pharmacologically intolerable salts, which can be obtained, for example, as process products during the preparation of the compounds according to the invention on an industrial scale, are converted into pharmacologically tolerable salts by processes known to the person skilled in the art. Those suitable are, on the one hand, water-soluble and water-insoluble acid addition salts with acids, such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are especially also suitable. Examples of basic salts are lithium, sodium, potassium, calcium, aluminium, magnesium, titanium, ammonium, meglumine or guanidinium salts, here, too, the bases being employed in salt preparation in an equimolar quantitative ratio or one differing therefrom.

Compounds of the formula I to be emphasized are those in which one of the substituents R1 and R2 is 1–4C-alkoxy, 3–5C-cycloalkoxy, 3–5C-cycloalkylmethoxy, benzyloxy or 1–4C-alkoxy which is completely or partially substituted by fluorine, and the other is 1–4C-alkoxy which is completely or partially substituted by fluorine, and R3 is phenyl, pyridyl, phenyl substituted by R31, R32 and R33 or pyridyl substituted by R34, R35, R36 and R37, where R31 is halogen, cyano, carboxyl, 1–4C-alkyl, 1–4C-alkoxy or 1–4C-alkoxycarbonyl, R32 is hydrogen, halogen, 1–4C-alkyl or 1–4C-alkoxy, R33 is hydrogen, halogen, 1–4C-alkyl or 1–4C-alkoxy, R34 is halogen or 1–4C-alkyl, R35 is hydrogen or halogen, R36 is hydrogen or halogen and R37 is hydrogen or halogen, the salts of these compounds, and the N-oxides of the pyridines and their salts.

Compounds of the formula I of embodiment a which are to be emphasized are those in which one of the substituents R1 and R2 is 1–4C-alkoxy, 3–5C-cycloalkoxy, 3–5C-cycloalkylmethoxy, benzyloxy or 1–4C-alkoxy which is completely or partially substituted by fluorine, and the other is 1–4C-alkoxy which is completely or partially substituted by fluorine, and R3 is phenyl, pyridyl, phenyl substituted by R31, R32 and R33 or pyridyl substituted by R34, R35, R36 and R37, where R31 is halogen, cyano, carboxyl, 1–4C-alkyl, 1–4C-alkoxy or 1–4C-alkoxycarbonyl,
R32 is hydrogen, halogen, 1–4C-alkyl or 1–4C-alkoxy,
R33 is hydrogen, halogen, 1–4C-alkyl or 1–4C-alkoxy,
R34 is halogen or 1–4C-alkyl,
R35 is hydrogen or halogen,
R36 is hydrogen or halogen and
R37 is hydrogen or halogen,
the salts of these compounds, and the N-oxides of the pyridines and their salts, where those compounds are excluded in which R1 is 1–4C-alkoxy which is completely or partially substituted by fluorine and R2 is 3–5C-cycloalkoxy.

Compounds of the formula I of embodiment b which are to be emphasized are those in which either
R1 is 1–4C-alkoxy which is completely or partially substituted by fluorine and
R2 is methoxy,
or
R1 is 1–4C-alkoxy, 3–5C-cycloalkoxy, 3–5C-cycloalkylmethoxy, benzyloxy or 1–4C-alkoxy which is completely or partially substituted by fluorine and
R2 is methoxy which is completely or partially substituted by fluorine,
or
R1 is 3–5C-cycloalkoxy, 3–5C-cycloalkylmethoxy or benzyloxy and
R2 is 1–4C-alkoxy which is completely or partially substituted by fluorine,
or
R1 is 1–4C-alkoxy which is completely or partially substituted by fluorine and
R2 is 3–5C-cycloalkylmethoxy or benzyloxy and
R3 is phenyl, pyridyl, phenyl substituted by R31, R32 and R33 or pyridyl substituted by R34, R35, R36 and R37, where
R31 is halogen, cyano, carboxyl, 1–4C-alkyl, 1–4C-alkoxy or 1–4C-alkoxycarbonyl,
R32 is hydrogen, halogen, 1–4C-alkyl or 1–4C-alkoxy,
R33 is hydrogen, halogen, 1–4C-alkyl or 1–4C-alkoxy,
R34 is halogen or 1–4C-alkyl,
R35 is hydrogen or halogen,
R36 is hydrogen or halogen and
R37 is hydrogen or halogen,
the salts of these compounds, and the N-oxides of the pyridines and their salts.

Compounds of the formula I which are particularly to be emphasized are those in which
one of the substituents R1 and R2 is 1–4C-alkoxy, 3–5C-cycloalkoxy, 3–5C-cycloalkylmethoxy, benzyloxy or 1–4C-alkoxy which is completely or partially substituted by fluorine, and the other is 1–4C-alkoxy which is completely or partially substituted by fluorine, and
R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and their salts.

Compounds of the formula I of embodiment a which are particularly to be emphasized are those in which one of the substituents R1 and R2 is 1–4C-alkoxy, 3–5C-cycloalkoxy, 3–5C-cycloalkylmethoxy, benzyloxy or 1–4C-alkoxy which is completely or partially substituted by fluorine, and the other is 1–4C-alkoxy which is completely or partially substituted by fluorine, and
R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and their salts, where those compounds are excluded in which R1 is 1–4C-alkoxy which is completely or partially substituted by fluorine and R2 is 3–5C-cycloalkoxy.

Compounds of the formula I of embodiment b which are particularly to be emphasized are those in which either
R1 is 1–4C-alkoxy which is completely or partially substituted by fluorine and
R2 is methoxy,
or
R1 is 1–4C-alkoxy, 3–5C-cycloalkoxy, 3–5C-cycloalkylmethoxy, benzyloxy or 1–4C-alkoxy which is completely or partially substituted by fluorine and
R2 is methoxy which is completely or partially substituted by fluorine,
or
R1 is 3–5C-cycloalkoxy, 3–5C-cycloalkylmethoxy or benzyloxy and
R2 is 1–4C-alkoxy which is completely or partially substituted by fluorine,
or
R1 is 1–4C-alkoxy which is completely or partially substituted by fluorine and
R2 is 3–5C-cycloalkylmethoxy or benzyloxy and
R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and their salts.

Preferred compounds of the formula I are, on the one hand, those in which
R1 is difluoromethoxy,
R2 is methoxy, ethoxy, isopropoxy, isobutoxy, cyclopentyloxy, cyclopropylmethoxy, cyclobutylmethoxy, difluoromethoxy or 2,2,2-trifluoroethoxy and
R3 is 2-bromophenyl, 2,6-dichloro-4-ethoxycarbonylphenyl, 2,6-dimethoxyphenyl, 4-cyano-2-fluorophenyl,
2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I are, on the other hand, those in which

R1 is methoxy, n-propoxy, n-butoxy, cyclopropylmethoxy or 2,2,2-trifluoroethoxy, R2 is difluoromethoxy and R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I of embodiment a are, on the one hand, those in which R1 is difluoromethoxy, R2 is methoxy, ethoxy, isopropoxy, isobutoxy, cyclopropylmethoxy, cyclobutylmethoxy, difluoromethoxy or 2,2,2-trifluoroethoxy and R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I of embodiment a are, on the other hand, those in which R1 is methoxy, n-propoxy, n-butoxy, cyclopropylmethoxy or 2,2,2-trifluoroethoxy, R2 is difluoromethoxy and R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I of embodiment b are, on the one hand, those in which R1 is difluoromethoxy, R2 is methoxy, cyclopropylmethoxy, cyclobutylmethoxy or difluoromethoxy and R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I of embodiment b are, on the other hand, those in which R1 is methoxy, n-propoxy, n-butoxy, cyclopropylmethoxy or 2,2,2-trifluoroethoxy, R2 is difluoromethoxy and R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Figure 2:
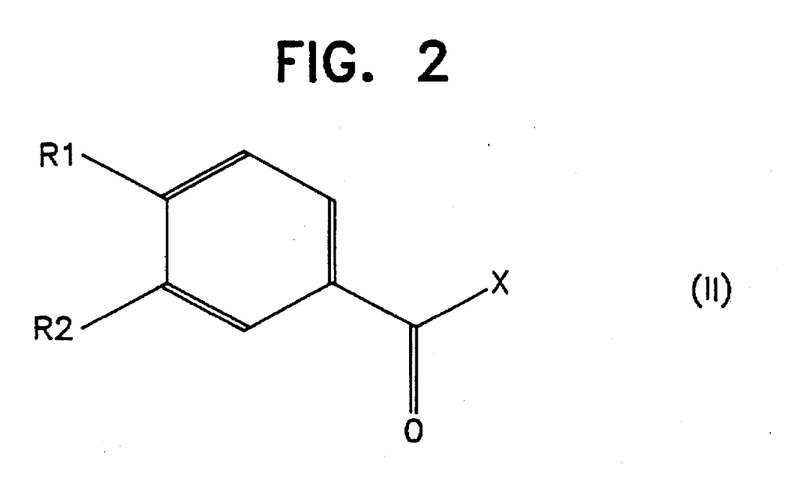

The invention further relates to a process for the preparation of the compounds of the formula I and their salts, and of the N-oxides of the pyridines and their salts. The process is characterized in that compounds of the formula II, in which R1 and R2 have the meanings indicated above and X is a suitable leaving group, are reacted with amines R3—NH$_2$, and in that, if desired, compounds of the formula I obtained are then converted into their salts and/or pyridines obtained are converted into the N-oxides and, if desired, then into the salts, or in that, if desired, salts of the compounds of the formula I obtained are then converted into the free compounds.

The person skilled in the art is familiar with suitable leaving groups X on the basis of his expert knowledge. For example, suitable acid halides of the formula II (X=Cl or Br) are used as starting materials. Otherwise, the reaction is carried out, for example, as described in the following examples or in a manner familiar per se to the person skilled in the art (e.g. as described in the International Patent Application WO 92/12961).

The N-oxidation is carried out in a manner likewise familiar to the person skilled in the art, e.g. with the aid of m-chloroperoxybenzoic acid in dichloromethane at room temperature. The person skilled in the art is familiar with the reaction conditions which are necessary for carrying out the process on the basis of his expert knowledge.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn, can be converted into salts. In this manner, pharmacologically non-tolerable salts can be converted into pharmacologically tolerable salts.

The compounds of the formula II and the amines R3-NH$_2$ are known, or can be prepared in a known manner.

The following examples illustrate the invention in greater detail, without restricting it. The compounds according to the invention and the starting compounds can be prepared in a manner analogous to that described in the examples.

EXAMPLES

Final Products

1. N-(3,5-Dichloropyrid-4-yl)-4-difluoromethoxy-3-methoxybenzamide 6.0 g of 4-difluoromethoxy-3-methoxybenzoic acid are heated at reflux in 40 ml of toluene with 19.6 g of thionyl chloride until the evolution of gas is complete. The solution is evaporated to dryness in vacuo and the residue is dissolved in about 60 ml of dry tetrahydrofuran. This solution is added dropwise at 15°–20° C. to a suspension—prepared from 4.9 g of 4-amino-3,5-dichloropyridine and 2.0 g of sodium hydride (80% strength in mineral oil) in 60 ml of dry tetrahydrofuran—with stirring and cooling. After stirring for one hour, the reaction mixture is acidified to pH 2 with 1N hydrochloric acid, the toluene/tetrahydrofuran phase is separated off and the aqueous phase is extracted a further 2 times with ethyl acetate. The combined organic phases are washed with saturated sodium hydrogen carbonate solution and water, dried over sodium sulphate and evaporated in vacuo. The residue is crystallized from isopropanol. Yield 5.8 g (58.6% of theory) of the title compound of m.p. 170° C.

Starting from the starting compounds described below, reaction of the appropriate benzoic acids with 4-amino-3,5-dichloropyridine, 4-amino-3,5-dichloro-2,6-difluoropyridine, 2,6-dichloroaniline, 2,6-dimethylaniline, 3-amino-2-chloropyridine, 2-amino-3,5-dibromopyridine, 4-amino-2,3,5,6-tetrafluoropyridine, 2,4,6-trifluoroaniline, 2,6-dichloro-4-ethoxycarbonylaniline, 2,6-difluoroaniline, 2-bromoaniline, 2-chloro-6-methylaniline, 2-methylaniline, 4-amino-3-chloro-2,5,6-trifluoropyridine or 2-amino-3-methylpyridine analogously to Example 1 gives the final products described below:

2. N-(3,5-Dichloropyrid-4-yl)-3,4-bis-difluoromethoxybenzamide (m.p.: 134° C.)
3. N-(3,5-Dichloropyrid-4-yl)-3-cyclobutylmethoxy-4-difluoromethoxybenzamide (m.p.: 155° C.)
4. N-(3,5-Dichloropyrid-4-yl)-3-cyclopentyloxy-4-difluoromethoxybenzamide (m.p.: 128.5°–129° C.)
5. N-(3,5-Dichloropyrid-4-yl)-3-cyclopropylmethoxy-4-difluoromethoxybenzamide (m.p.: 158° C.)
6. N-(3,5-Dichloro-2,6-difluoropyrid-4-yl)-3-difluoromethoxy-4-methoxybenzamide (m.p.: 218° C.)
7. N-(2,6-Dichlorophenyl)-3-difluoromethoxy-4-methoxybenzamide (m.p.: 164° C.)
8. N-(2,6-Dimethylphenyl)-3-difluoromethoxy-4-methoxybenzamide (m.p.: 164° C.)
9. N-(2-Chloropyrid-3-yl)-3-difluoromethoxy-4-methoxybenzamide (m.p.: 165° C.)
10. N-(3,5-Dibromopyrid-2-yl)-3-difluoromethoxy-4-methoxybenzamide (m.p.: 143° C.)
11. N-(3,5-Dichloropyrid-4-yl)-3-difluoromethoxy-4-methoxybenzamide (m.p.: 178° C.)
12. N-(3,5-Dichloropyrid-4-yl) -3-difluoromethoxy-4-propoxybenzamide (m.p.: 159° C.)
13. N-(3,5-Dichloropyrid-4-yl)-3-ethoxy-4-difluoromethoxybenzamide (m.p.: 134° C.)
14. N-(3,5-Dichloropyrid-4-yl) -benzyloxy-3-difluoromethoxybenzamide (m.p.: 152° C.)
15. N-(3,5-Dichloropyrid-4-yl)-4-butoxy-3-difluoromethoxybenzamide (m.p.: 146° C.)
16. N-(3,5-Dichloropyrid-4-yl)-4-cyclopropylmethoxy-3-difluoromethoxybenzamide (m.p.: 159° C.)
17. N-(3,5-Dichloropyrid-4-yl)-4-difluoromethoxy-3-(1-methylethoxy)benzamide (m.p.: 99.5° C.)
18. N-(3,5-Dichloropyrid-4-yl)-4-difluoromethoxy-3-(2,2,2-trifluoroethoxy)benzamide (m.p.: 147° C.)
19. N-(3,5-Dichloropyrid-4-yl)-4-difluoromethoxy-3-(2-methylpropoxy)benzamide (m.p.: 153° C.)
20. N-(2,3,5,6-Tetrafluoropyrid-4-yl)-4-difluoromethoxy-3-methoxybenzamide (m.p.: 146° C.)
21. N-(2,4,6-Trifluorophenyl)-4-difluoromethoxy-3-methoxybenzamide (m.p.: 145° C.)
22. N-(2,6-Dichloro-4-ethoxycarbonylphenyl)-4-difluoromethoxy-3-methoxybenzamide (m.p.: 176° C.)
23. N-(2,6-Dichlorophenyl)-4-difluoromethoxy-3-methoxybenzamide (m.p.: 186° C.)
24. N-(2,6-Difluorophenyl)-4-difluoromethoxy-3-methoxybenzamide (m.p. 139° C.)
25. N-(2,6-Dimethylphenyl)-4-difluoromethoxy-3-methoxybenzamide (m.p.: 143° C.)
26. N-(2-Bromophenyl)-4-difluoromethoxy-3-methoxybenzamide (m.p.: 121° C.)
27. N-(2-Chloro-6-methylphenyl)-4-difluoromethoxy-3-methoxybenzamide (m.p.: 144° C.)
28. N-(2-Chloropyrid-3-yl)-4-difluoromethoxy-3-methoxybenzamide (m.p.: 137.5° C.)
29. N-(2-Methylphenyl)-4-difluoromethoxy-3-methoxybenzamide (m.p.: 125° C.)
30. N-(3,5-Dibromopyrid-2-yl)-4-difluoromethoxy-3-methoxybenzamide (m.p.: 141° C.)
31. N-(3,5-Dichloro-2,6-difluoropyrid-4-yl)-4-difluoromethoxy-3-methoxybenzamide (m.p.: 174° C.)
32. N-(3-Chloro-2,5,6-trifluoropyrid-4-yl)-4-difluoromethoxy-3-methoxybenzamide (m.p.: 141° C.)
33. N-(3-Methylpyrid-2-yl)-4-difluoromethoxy-3-methoxybenzamide (m.p.: 96° C.)

Starting Compounds

A. 4-Difluoromethoxy-3-methoxybenzoic acid

A solution of 7.3 g of 80% strength sodium chlorite in 15 ml of water is added dropwise with continuous stirring to a mixture of 10.0 g of 4-difluoromethoxy-3-methoxybenzaldehyde, 6.5 g of sulphamic acid and 50 ml of glacial acetic acid. The internal temperature is kept between 30° and 35° C. by cooling with ice water. After dropwise addition is complete, the mixture is stirred for a further 1 h and then diluted with water. The precipitated 4-difluoromethoxy-3-methoxybenzoic acid is filtered off with suction, washed with water, dried in vacuo and crystallized from acetonitrile/petroleum ether (b.p. 40°) 2/8. Yield 7.1 g; m.p. 170° C.

The following benzoic acids are obtained analogously:
3,4-Bis(difluoromethoxy) benzoic acid (m.p.: 104.5° C.)
3-Cyclobutylmethoxy-4-difluoromethoxybenzoic acid (m.p.: 132° C.)
3-Cyclopentyloxy-4-difluoromethoxybenzoic acid (m.p.: 125.5° C.)
3-Cyclopropylmethoxy-4-difluoromethoxybenzoic acid (m.p.: 118°–118.5° C.)
3-Ethoxy-4-difluoromethoxybenzoic acid (m.p.: 157° C.)
4-Difluoromethoxy-3-(1-methyl)ethoxybenzoic acid (m.p.: 93° C.)
4-Difluoromethoxy-3-(2,2,2-trifluoroethoxy)benzoic acid (m.p.: 109° C.)
3-Difluoromethoxy-4-methoxybenzoic acid (m.p.: 178° C.)
3-Difluoromethoxy-4-propoxybenzoic acid (m.p.: 148° C.)
4-Benzyloxy-3-difluoromethoxybenzoic acid (m.p.: 169° C.)
4-Butoxy-3-difluoromethoxybenzoic acid (m.p.: 136° C.)
4-Cyclopropylmethoxy-3-difluoromethoxybenzoic acid (m.p.: 150° C.)

B. 4-Difluoromethoxy-3-methoxybenzaldehyde

Chlorodifluoromethane is introduced into a mixture of 200 g of vanillin, 6.7 g of benzyltrimethylammonium chloride, 314 g of 50% strength sodium hydroxide solution and 2 liters of dioxane with vigorous stirring for about 2 h. The mixture is then partitioned between ice water and ethyl acetate, the organic phase is separated off, the aqueous phase is extracted twice by stirring with ethyl acetate, and the combined organic phases are dried over magnesium sulphate and concentrated in vacuo. To remove unreacted vanillin, the oil is chromatographed on neutral silica gel using toluene. After evaporating the eluate, 249 g of 4-difluoromethoxy-3-methoxybenzaldehyde are obtained as an oil.

The following benzaldehydes are obtained analogously:

3-Cyclobutylmethoxy-4-difluoromethoxybenzaldehyde (m.p.: 46° C.)

3-Cyclopropylmethoxy-4-difluoromethoxybenzaldehyde (oil)

4-Difluoromethoxy-3-(1-methyl)ethoxybenzaldehyde (oil)

4-Difluoromethoxy-3-(2,2,2-trifluoroethoxy)benzaldehyde (oil)

3,4-Bis(difluoromethoxy)benzaldehyde (oil)

3-Cyclopentyloxy-4-difluoromethoxybenzaldehyde (oil)

3-Ethoxy-4-difluoromethoxybenzaldehyde (oil)

4-Difluoromethoxy-3-(2-methylpropoxy)benzaldehyde (oil)

3-Difluoromethoxy-4-methoxybenzaldehyde (m.p.: 41° C.)

3-Difluoromethoxy-4-propoxybenzaldehyde (oil)

4-Benzyloxy-3-difluoromethoxybenzaldehyde (m.p.: 52°–52.5° C.)

4-Butoxy-3-difluoromethoxybenzaldehyde (oil)

4-Cyclopropylmethoxy-3-difluoromethoxybenzaldehyde (oil)

Commercial Utility

The compounds according to the invention have useful pharmacological properties which make them industrially utilizable. As cyclic nucleotide phosphodiesterass (PDE) inhibitors (specifically of type IV), they are suitable on the one hand as bronchial therapeutics (for the treatment of airway obstructions on account of their dilating action but also on account of their respiratory rate- or respiratory drive-increasing action), but on the other hand especially for the treatment of disorders, in particular of an inflammatory nature, e.g. of the airways (asthma prophylaxis), of the skin, of the intestine, of the eyes and of the joints, which are mediated by mediators such, as histamine, PAF (platelet-activating factor), arachidonic acid derivatives such, as leukotrienes and prostaglandins, cytokines, interleukins IL-1 to IL-12, alpha-, beta- and gamma-interferon, tumour necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma); dermatoses (especially of proliferative, inflammatory and allergic type), such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous ache, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS), types of shock [septic shock, endotoxin shock, gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as colics of the kidneys and of the ureters in connection with kidney stones.

The invention further relates to a method for the treatment of mammals, including humans, which are suffering from one of the abovementioned illnesses. The method is characterized in that a therapeutically active and pharmacologically tolerable amount of one or more of the compounds according to the invention is administered to the ill mammal.

The invention further relates to the compounds according to the invention for use in the treatment and/or prophylaxis of the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarily between 0.01 and 0.5 mg/kg. The customary dose in the case of systemic therapy is between 0.05 and 2 mg per day.

Biological Investigations

In the investigation of PDE IV inhibition on the cellular plane, the activation of inflammatory cells is ascribed particular importance. An example is FMLP (N-formylmethionylleucylphenylalanine)-induced superoxide production of neutrophilic granulocytes, which can be measured as luminol-amplified chemoluminescence. (Mc Phail L C, Strum S L, Leone P A and Sozzani S, The neutrophil respiratory burst mechanism. In "Immunology Series" 57: 47–76, 1992; ed. Coffey R G (Marcel Decker, Inc., New York-Basle-Hong Kong)).

Substances which inhibit chemoluminescence and cytokine secretion and the secretion of proinflammatory mediators on inflammatory cells, in particular neutrophilic and eosinophilic granylocytes, are those which inhibit PDE IV. This isoenzyme of the phosphodiesterase families is particularly represented in granulocytes. Its inhibition leads to an increase in the intracellular cyclic AMP concentration and thus to the inhibition of cellular activation. PDE IV inhibition by the substances according to the invention is thus a central indicator for the suppression of inflammatory processes. (Giembycz M A, Could isoenzyme-selective phosphodiesterase inhibitors render bronchodilatory therapy redundant in the treatment of bronchial asthma?. Biochem Pharmacol 43: 2041–2051, 1992; Torphy T J et al., Phosphodiesterase inhibitors: new opportunities for treatment of asthma. Thorax 46: 512–523, 1991; Schudt C et al., Zardaverine: a cyclic AMP PDE III/IV inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and Ca$_i$. Naunyn-Schmiedebergs Arch Pharmacol 344: 682–690, 1991; Nielson C P et al., Effects of selective phosphodiesterase inhibitors on polymorphonuclear leucocyte respiratory burst. J Allergy Clin Immunol 86: 801–808, 1990; Schade et al., The specific type III and IV phosphodiesterase inhibitor zardaverine suppresses formation of tumor necrosis factor by macrophages. European Journal of Pharmacology 230: 9–14, 1993).

1. Inhibition of PDE IV activity

Methodology

The activity test was carried out according to the method of Bauer and Schwabe, which was adapted to microtitre plates (Naunyn-Schmiederberg's Arch. Pharmacol. 311, 193–198, 1980). In this test, the PDE reaction is carried out in the first step. In a second step, the resultant 5'-nucleotide is cleaved to the uncharged nucleoside by a snake venom 5'-nucleotidase from *Ophiophagus hannah* (King Cobra). In the third step, the nucleoside is separated from the remaining charged substrate on ion exchange columns. The columns are eluted directly into minivials using 2 ml of 30 mM ammonium formate (pH 6.0), to which a further 2 ml of scintillation fluid is added for counting.

The inhibitory values determined for the compounds according to the invention follow from the following Table 1, in which the numbers of the compounds correspond to the numbers of the examples.

TABLE 1

| Inhibition of PDE IV activity | |
|---|---|
| Compound | –log IC$_{50}$ |
| 1 | 8.64 |
| 2 | 8.42 |
| 3 | 8.74 |
| 4 | 9.18 |

2. Effect of dyspnoea and migration of proinflammatory (immunocompetent) cells from the blood vessels into the airway lumen after allergic reaction of conscious guinea-pigs Immunocompetent blood cells (leucocytes) appear in the airway lumens under the influence of allergic, inflammatory reactions. This pathological migration can support itself, i.e. lead to chronic changes, and plays an important part as a pathological mechanism of chronic airway obstruction (of asthma) but also of allergic rhinitis and/or conjunctivitis. The inhibition of the migration by pharmaceuticals is an important therapeutic principle and is a measure of antiallergic or antiinflammatory actions.

The experimental animal methodology employed for the measurement of the acute effect of an allergic reaction on respiration and cell migration itself essentially follows the descriptions of P. A. Hutson et al. (Am. Rev. Respir. Dis., 137, 548, 1988) and J. P. Tarayre et al. (J. Parmacol. Meth., 23, 13, 1990) and also R. Beume et al. (Atemw. Lungenkrkh., 11, 324, 1985).

A defined guinea-pig collective is sensitized intraperitoneally to ovalbumin (20 µg+20 mg of Al(OH)$_3$). 14 days later, the animals are tested:

–1 h treatment orally, 0 h provocation of the allergic reaction, thoracographic latency time measurement until occurrence of dyspnoea, non-occurrence=protective action.

+1 h treatment orally,

+24 h anaesthesia and bronchoalveolar lavage: Determination of the total cell number, counting of the differential cell picture in the lavage, determination of the protein content in the cell-free supernatant of the lavage.

The controlled used in each case was 1 random sample of sensitized animals: Placebo treatment+sham provocation or placebo treatment+provocation.

The compound of Example 1 (=compound 1), 30 µmol/kg p.o., acts on the parameters of this relation as follows:

| | Placebo + sham provocation | Placebo + provocation | Compound 1 + provocation |
|---|---|---|---|
| N, of which protected | 15<br>15 | 13<br>2 | 14<br>8 |
| | Total leucocytes (× 10$^6$/10 ml) | | |
| Median<br>min./max. | 2.2 (1)<br>1.1–3.8 | 9.8 (4.5)<br>1.0–21.4 | 2.5 (1.1)<br>1.5–4.2 |
| | Neutrophilic granulocytes (× 10$^6$/10 ml) | | |
| Median<br>min./max. | 0.04 (1)<br>0.01–0.1 | 0.44 (11)<br>0.01–1.1 | 0.0 (0)<br>0.0–0.08 |

|  | Placebo + sham provocation | Placebo + provocation | Compound 1 + provocation |
|---|---|---|---|
| Eosinophilic granulocytes ($\times 10^6/10$ ml) | | | |
| Median | 0.8 (1) | 5.8 (7.3) | 1.2 (1.5) |
| min./max. | 0.4–1.8 | 0.3–14.5 | 0.6–2.5 |
| Macrophages ($\times 10^6/10$ ml) | | | |
| Median | 1.5 (1) | 3.2 (2.1) | 1.2 (0.8) |
| min./max. | 0.8–2.3 | 0.7–6.2 | 0.9–2.3 |
| Protein content (mg/10 ml) | | | |
| Median | 3.7 (1) | 8.8 (2.4) | 4.1 (1.1) |
| min./max. | 2.3–4.9 | 3.4–22.0 | 2.6–11.0 |

No animal reacts to the sham provocation, 2 animals do not develop any dyspnoea despite provocation with ovalbumin=spontaneously protected, and 8 animals do not react with substance=protected.

Provocation, i.e. the triggering of an allergic reaction, increases the passage of cells and protein distinctly, even if with great scattering. Compound 1 inhibits these passages to base values (placebo+sham provocation).

I claim:

1. A compound of formula I in which
- R1 is 1–4C-alkoxy which is completely or partially substituted by fluorine,
- R2 is 3–5C-cycloalkylmethoxy or benzyloxy, and
- R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, a salt thereof, and the N-oxide of a pyridine or a salt thereof.

2. A compound of claim 1, in which
- R1 is difluoromethoxy,
- R2 is cyclopropylmethoxy and
- R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, a salt thereof, and the N-oxide of a pyridine or a salt thereof.

3. A medicament composition containing an effective amount of a compound according to claim 1 and a suitable carrier therefor.

4. A method which comprises administering an effective amount of a phosphodiesterase (PDE) inhibitor to a subject in need of such therapy and wherein the phosphodiesterase inhibitor is a pharmacologically acceptable compound of claim 1.

5. In a method of compounding a medicament composition comprising a suitable carrier and an effective amount of an active component for treating an airway disorder, the improvement wherein the active component is a compound of claim 1.

6. In a method of compounding a medicament composition having a suitable carrier and an effective amount of a component for treating a dermatosis, the improvement wherein the active component is a compound of claim 1.

7. A compound of claim 2, wherein R3 is 3,5-dichloropyrid-4-yl, a salt thereof, an N-oxide thereof or a salt of an N-oxide thereof.

8. A compound of claim 1 wherein
- R1 is difluoromethoxy,
- R2 is cyclobutylmethoxy and
- R3 is 3,5-dichloropyrid-4-yl, a salt thereof, an N-oxide thereof or a salt of an N-oxide thereof.

* * * * *

UNITED STATES PATENT AND TRADEMARK OFFICE
CERTIFICATE OF CORRECTION

PATENT NO. : 5,712,298

DATED : January 27, 1998

INVENTOR(S) : AMSCHLER

It is certified that error appears in the above-identified patent and that said Letters Patent is hereby corrected as shown below:

Title page, right column, ABSTRACT, line 9, "trifluoromethyl" should read --trifluoromethyl,--.
Column 1, line 56, "alkyl" should read --1-4C-alkyl--.
Column 3, line 61, "6-methylphenol" should read --6-methylphenyl--. Column 4, line 13, "tolerable." should read --tolerable--.
Column 8, line 35, change "mariner" to --manner--.
Column 11, line 34, "phosphodiesterass" should read --phosphodiesterase--; line 43, "such," should read --, such--; line 44, "such," should read --, such--; line 65, "ache" should read --acne--. Column 14, Table 1, last line, "4" should read --5--. Column 16, line 1, "and" should read --or--; line 15, "and" should read --or--.

Signed and Sealed this

Twenty-eighth Day of April, 1998

Attest:

*Attesting Officer*

BRUCE LEHMAN

*Commissioner of Patents and Trademarks*